(12) United States Patent
Zhao

(10) Patent No.: US 7,771,705 B2
(45) Date of Patent: Aug. 10, 2010

(54) RADIOGRAPHIC CONTRASTING AGENTS AND RADIO-OPAQUE POLYMERIC MATERIALS FOR MEDICAL DEVICES

(75) Inventor: Jonathon Z. Zhao, Belle Mead, NJ (US)

(73) Assignee: cordis Corporation, Miami Lakes, FL (US)

( * ) Notice: Subject to any disclaimer, the term of this patent is extended or adjusted under 35 U.S.C. 154(b) by 0 days.

(21) Appl. No.: 12/412,052

(22) Filed: Mar. 26, 2009

(65) Prior Publication Data

US 2009/0209745 A1   Aug. 20, 2009

Related U.S. Application Data

(63) Continuation of application No. 11/301,874, filed on Dec. 13, 2005, now abandoned.

(51) Int. Cl.
*A61K 49/00* (2006.01)
*A61K 49/04* (2006.01)

(52) U.S. Cl. .......................................... 424/9.1; 424/9.4
(58) Field of Classification Search ....................... None
See application file for complete search history.

(56) References Cited

U.S. PATENT DOCUMENTS

| | | | |
|---|---|---|---|
| 5,451,393 | A | 9/1995 | Liversidge et al. |
| 6,426,145 | B1 | 7/2002 | Moroni |
| 6,599,448 | B1 | 7/2003 | Ehrhard et al. |
| 6,852,308 | B2 | 2/2005 | Kohn et al. |
| 2001/0031035 | A1 | 10/2001 | Salb et al. |

FOREIGN PATENT DOCUMENTS

| | | | |
|---|---|---|---|
| EP | 0557345 | B1 | 9/1993 |
| EP | 1588725 | A1 | 3/2005 |
| EP | 1586337 | A2 | 4/2005 |
| EP | 1702628 | A2 | 9/2006 |
| WO | WO 01/87372 | A1 | 11/2001 |
| WO | WO 2004/112864 | A2 | 12/2004 |

OTHER PUBLICATIONS

Davy, K.W.M et al. "X-Ray Opaque Methacrylate Polymers for Biomedical Applications" Polymer International, vol. 43, No. 2, 1997, pp. 143-154.

Ginebra M.P. et al., "Improvement of the mechanical properties of acrylic bone cements by substitution of the radio-opaque agent" Journal of Materials Science: Materials in Medicine, vol. 10, 1999, pp. 733-737.

Okamura M. et al. "Synthesis and properties of radiopaque polymer hydrogels: polyion complexes of copolymers of acrylamide derivatives having triiodophenyl and carboxyl groups and *p* -styrene sulfonate and polyallylamine" Journal of Molecular Structure, vol. 554, 2000, pp. 35-45.

International Search Report re: EP06256292 dated Nov. 26, 2007.

*Primary Examiner*—Michael G Hartley
*Assistant Examiner*—Melissa Perreira

(57) ABSTRACT

The present invention discloses a radiographic contrasting agent containing multiple aromatic groups, each of which is substituted with at least three halogen atoms. The radiographic contrasting agent can initiate a polymerization process. The present invention also discloses a radio-opaque polymeric material that comprises a biodegradable polymer having at least one radiographic contrasting moiety covalently attached thereto. The radio-opaque polymeric material provides enhanced contrasting intensity in radiographic imaging. The radio-opaque polymeric material can be applied on at least a portion of one surface of a medical device. The radio-opaque polymeric material can also be used to construct a medical device, a component thereof, or a portion of a component thereof.

1 Claim, No Drawings

RADIOGRAPHIC CONTRASTING AGENTS AND RADIO-OPAQUE POLYMERIC MATERIALS FOR MEDICAL DEVICES

CROSS-REFERENCE TO RELATED APPLICATION

This application is a Continuation of U.S. application Ser. No. 11/301,874, filed Dec. 13, 2005 now abandoned.

FIELD OF INVENTION

The present invention relates to a radiographic contrasting agent that can initiate a polymerization process and a radio-opaque polymeric material comprising a biodegradable polymer having at least one radiographic contrasting moiety covalently attached thereto.

BACKGROUND OF INVENTION

Biodegradable polymers have been widely used to construct medical devices, particularly implantable medical devices. Compared to the conventional metallic material, biodegradable polymers offer many advantages. First, biodegradable polymers are conformable and flexible, thereby causing less stress to the biological tissues. Second, medical implants made from biodegradable polymers do not require a second surgical intervention for removal. Third, the biodegradable polymers may be used to enhance the therapeutic effect of a medical implant. For example, a fractured bone that has been fixated with a rigid metal implant has a tendency for refracture upon removal of the metal implant because the stress is borne by the rigid metal, so the bone has not been able to carry sufficient load during the healing process. In contrast, a biodegradable polymer can be tuned to degrade at a certain rate so that an implant prepared therefrom will slowly transfer load to the healing bone. In addition, biodegradable polymers are useful in drug delivery systems. For example, a therapeutic agent can be admixed with a biodegradable polymer to form a polymer matrix. The release rate of the therapeutic agent in such a polymer matrix can be controlled by adjusting the degradation rate of the biodegradable polymer.

Biodegradable polymers can be either natural or synthetic. In general, synthetic polymers offer greater advantages than natural materials since the synthetic polymers can be tailored to give the desirable properties according to their intended use. Synthetic polymers also offer better consistency and uniformity than natural polymers do. Furthermore, unlike natural materials, synthetic polymers cause little immunogenic responses after implantation. Common synthetic biodegradable polymers include polyglycolide, polylactide, poly(lactide-co-glycolide), polydioxanone, polycaprolactone, poly(hydroxyl butyrate), poly(trimethylene carbonate), polyphosphoester, polyphosphazene, and other poly(esteramide).

However, most biodegradable polymers are not radio-opaque. Consequently, medical devices made from those biodegradable polymers cannot be visualized by means of radiographic imaging. The ability to see the radiographic image of a medical device being used in, or implanted within, the body is very important since radiographic imaging provides a physician the ability to monitor and adjust the medical device during operation. For some medical implant applications, X-ray visibility is mandatory.

To achieve desirable radio-opacity in polymeric materials, one conventional method utilizes inorganic radiographic contrasting agents, such as barium sulfate, zirconium dioxide, or bismuth halides as additives or fillers in the polymeric material to form a radio-opaque polymeric matrix. However, these inorganic agents do not mix well with polymeric materials and may cause phase separation in the radio-opaque polymeric matrix. The phase separation problem is further aggravated since high concentrations (around 10%, and often times 20-30% by weight) of these inorganic radiographic contrasting agents are routinely used to obtain the required radio-opacity. The incompatibility between the polymeric and inorganic phases compromises the physicomechanical properties of the polymer matrix. Another disadvantage of using inorganic radiographic contrasting agents is the toxicity to tissues caused by the leach-out of these inorganic agents.

An alternative approach to introduce radio-opacity into polymeric materials is to synthesize polymers having covalently bound bromine or iodine atoms that may produce a radiographic contrasting effect (See U.S. Pat. No. 6,426, 145). One radio-opaque composition of the prior art comprises a polymer having a non-leachable radio-opaque moiety covalently attached to the polymer (See U.S. Pat. No. 6,599, 448), wherein the non-leachable radio-opaque moiety includes halogen substituted aromatic groups. The prior art has also disclosed a radio-opaque polymeric material comprising a diphenol-based monomer unit substituted with at least one bromine or iodine atom (See U.S. Pat. No. 6,852, 308). However, preparations of these prior art radio-opaque polymers require synthesis of radiographic contrasting monomer units, which may increase the technical complexity and production cost.

Thus, there remains a need for a non-leachable radiographic contrasting agent that can provide enhanced contrasting intensity and a radio-opaque polymeric material that can be readily prepared from such a non-leachable radiographic contrasting agent and common biodegradable monomers.

SUMMARY OF THE INVENTION

Accordingly, the present invention provides a radiographic contrasting agent comprising a monosaccharide backbone or an aliphatic or alicyclic backbone of 2 to 12 carbon atoms, a reactive nucleophilic group, and at least two halogen-substituted aromatic groups, wherein each of the at least two halogen-substituted aromatic groups is substituted with at least three halogen atoms and is covalently attached to the monosaccharide backbone or the aliphatic or alicyclic backbone through a linkage group, wherein the linkage group is oxygen, sulfur, —NH—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, or triazole.

Preferably, the radiographic contrasting agent has the following structure:

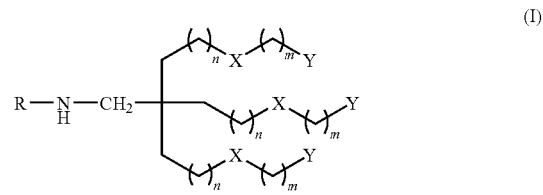

(I)

wherein R is a hydrogen atom, or an alkyl group having 1 to 4 carbon atoms;

X is oxygen, sulfur, —NH, —O(CO)—, —(CO)O—, —NH(CO)—, —(CO)NH—, —O(SO$_2$)—,

—(SO$_2$)O—, —O(SO)—, —(SO)O—, —NH(SO$_2$)—, —(SO$_2$)NH—, —NH(SO)—, —(SO)NH—, or triazole; Y is an aromatic group substituted with at least three halogen atoms; n and m are the same or different, and are independently zero or an integer of 1 to 4. Preferably, R is hydrogen; X is —O(CO)—, —NH(CO)—, or triazole; and n and m are both zero.

The present invention also provides a radio-opaque polymeric material, comprising a biodegradable polymer having at least one radiographic contrasting moiety covalently attached thereto, wherein the at least one radiographic contrasting moiety is covalently attached to the biodegradable polymer through a functional group derived from a nucleophilic reaction, and the at least one radiographic contrasting moiety comprises a monosaccharide backbone or an aliphatic or alicyclic backbone of 2 to 12 carbon atoms, and at least two halogen-substituted aromatic groups, wherein each of the at least two halogen-substituted aromatic groups is substituted with at least three halogen atoms and is covalently attached to the monosaccharide backbone or the aliphatic or alicyclic backbone through a linkage group, wherein the linkage group is oxygen, sulfur, —NH—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, or triazole.

Preferably, R is hydrogen; X is —O(CO)—, —NH(CO)—, or triazole; and n and m are both zero.

Preferably, the radiographic contrasting moiety covalently attached to the biodegradable polymer has the following structure:

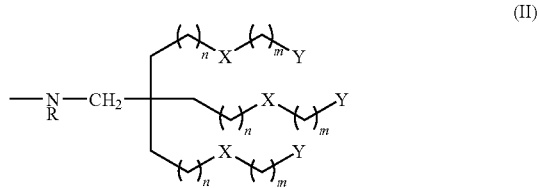

(II)

wherein R is a hydrogen atom, or an alkyl group having 1 to 4 carbon atoms;

X is oxygen, sulfur, —NH, —O(CO)—, —(CO)O—, —NH(CO)—, —(CO)NH—, —O(SO$_2$)—,

—(SO$_2$)O—, —O(SO)—, —(SO)O—, —NH(SO$_2$)—, —(SO$_2$)NH—, —NH(SO)—, —(SO)NH—, or triazole; Y is an aromatic group substituted with at least three halogen atoms; n and m are the same or different, and are independently zero or an integer of 1 to 4.

In another aspect, the present invention provides a medical device, wherein at least one portion of the medical device is radio-opaque, the at least one radio-opaque portion of the medical device comprising a radio-opaque polymeric material, which comprises a biodegradable polymer having at least one radiographic contrasting moiety covalently attached thereto, wherein the at least one radiographic contrasting moiety is covalently attached to the biodegradable polymer through a functional group derived from a nucleophilic reaction, and the at least one radiographic contrasting moiety comprises a monosaccharide backbone or an aliphatic or alicyclic backbone of 2 to 12 carbon atoms, a reactive nucleophilic group, and at least two halogen-substituted aromatic groups, wherein each of the at least two halogen-substituted aromatic groups is substituted with at least three halogen atoms and is covalently attached to the monosaccharide backbone or the aliphatic or alicyclic backbone through a linkage group, wherein the linkage group is oxygen, sulfur, —NH—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, or triazole.

DETAILED DESCRIPTION OF THE INVENTION

The present invention provides a radiographic contrasting agent comprising a monosaccharide backbone or an aliphatic or alicyclic backbone of 2 to 12 carbon atoms, a reactive nucleophilic group, and at least two halogen-substituted aromatic groups. By "monosaccharide", it is meant a simple sugar that cannot be hydrolyzed to smaller units. Empirical formula for monosaccharide is $(CH_2O)_n$, wherein n is an integer of 1 to 9. As used herein, "an aliphatic backbone" denotes an organic moiety consisting of carbon atoms linked in open chains, and "an alicyclic backbone" denotes an organic moiety consisting of carbon atoms forming one or more rings that are not aromatic. The aliphatic or alicyclic backbone of the present invention contains 2 to 12 carbon atoms. By "a reactive nucleophilic group", it is meant a reactive chemical moiety having an affinity to atomic nuclei. Reactive nucleophilic groups suitable for the present invention include, but are not limited to: NRH, OH, and SH; wherein R is a hydrogen atom or an alkyl group having 1 to 4 carbon atoms. Each of the at least two halogen-substituted aromatic groups in the inventive radiographic contrasting agent is substituted with at least three halogen atoms and is covalently attached to the monosaccharide backbone or the aliphatic or alicyclic backbone through a linkage group. The linkage group is selected from oxygen, sulfur, —NH—, —O(CO)—, —(CO)O—,

—NH(CO)—, —(CO)NH—, —O(SO$_2$)—, —(SO$_2$)O—, —O(SO)—, —(SO)O—, —NH(SO$_2$)—,

—(SO$_2$)NH—, —NH(SO)—, —(SO)NH—, and triazole. As used herein, "(CO)" denotes a carbonyl moiety; "(SO)" denotes a sulfinyl moiety; and "(SO$_2$)" denotes a sulfonyl moiety. The linkage group links the monosaccharide backbone or aliphatic or alicyclic backbone and the at least two halogen-substituted aromatic groups through covalent bonds.

The linkage group expressed as "-linkage-" denotes a linkage in the manner as follows: (the monosaccharide backbone or the aliphatic or alicyclic backbone)-linkage-(one of the at least two halogen-substituted aromatic groups). For example, "—(CO)O—" denotes a linkage as follows: (the monosaccharide backbone or the aliphatic or alicyclic backbone)—(CO)O—(one of the at least two halogen-substituted aromatic groups). Preferably, the linkage group of the present invention is —NH(CO)—, —O(CO)—, or triazole. The term "triazole" as used herein includes both 1,2,3-triazole and 1,2,4-triazole. When the linkage group is triazole, the monosaccharide backbone or the aliphatic or alicyclic backbone and the at least two halogen-substituted aromatic group are linked through one of the two carbon atoms, and the nitrogen atom at the 4 position in the case of 1,2,4-triazole or the nitrogen atom at the 3 position in the case of 1,2,3-triazole.

The monosaccharide backbones suitable for the present invention include, but are not limited to: monose, diose, triose, tetrose, pentose, hexose, heptose, octose, and nonose. Preferably, the monosaccharide backbone of the present invention contains 3 to 7 carbon atoms. The aliphatic backbones suitable for the present invention include, but are not limited to: ethyl, n-propyl, iso-propyl, n-butyl, sec-butyl, n-pentyl, n-hexyl, n-heptyl, n-octyl, and analogs or isomers thereof. The alicyclic backbones suitable for the present invention include, but are not limited to: cyclobutyl, cyclopentyl, cyclohexyl, cycloheptyl, cyclooctyl, cyclobutene, cyclopentene, cyclohexene, cycloheptene, cyclooxtanene, and analogs or isomers thereof. Preferably, the aliphatic or alicyclic backbone is an aliphatic or alicyclic moiety having 4 to 8 carbon atoms.

It is preferable that the radiographic contrasting agent of the present invention contains at least three halogen-substituted aromatic groups. By "a halogen-substituted aromatic group", it is meant an aromatic group having at least one halogen substituent. By "an aromatic group", it is meant a cyclic organic compound containing multiple conjugated double bonds. The halogen-substituted aromatic group of the present invention may be halogen-substituted carbocyclic, heterocyclic, or polycyclic compounds. Halogen-substituted aromatic groups suitable for the present invention include, but are not limited to: halogen-substituted benzene, toluene, xylenes, styrenes, pyridine, furan, naphthalene, anthracene, phenanthrene, indole, quinoline, and isoquinoline. Preferably, the halogen-substituted aromatic group of the present invention is halogen-substituted benzene. Each of the halogen-substituted aromatic groups of the present invention is substituted with at least three halogen atoms. Preferably, the at least three halogen atoms are bromine, iodine, or combinations thereof. More preferably, the halogen-substituted aromatic group of the present invention is substituted with at least three iodine atoms. In one preferred embodiment of the present invention, the halogen-substituted aromatic group is 2,3,5-triiodobenzene.

Preferably, the radiographic contrasting agent of the present invention has the following structure:

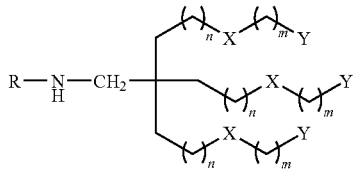
(I)

wherein R is a hydrogen atom, or an alkyl group having 1 to 4 carbon atoms;

X is oxygen, sulfur, —NH, —O(CO)—, —(CO)O—, —NH(CO)—, —(CO)NH—, —O(SO$_2$)—,

—(SO$_2$)O—, —O(SO)—, —(SO)O—, —NH(SO$_2$)—, —(SO$_2$)NH—, —NH(SO)—, —(SO)NH—, or triazole; Y is an aromatic group substituted with at least three halogen atoms; n and m are the same or different, and are independently zero or an integer of 1 to 4. The alkyl groups suitable for the present invention include, but are not limited to: methyl, ethyl, n-propyl and n-butyl. Preferably, R is a hydrogen atom. More preferably, R is a hydrogen atom and X is —O(CO)—, —NH(CO)—, or triazole. Most preferably, R is a hydrogen atom; X is —O(CO)—, —NH(CO)—, or triazole; and m and n are both zero. It is preferable that the aromatic group substituted with at least three halogen atoms is a benzene group substituted with at least three halogen atoms. It is also preferable that the at least three halogen atoms are bromine, iodine, or combinations thereof. It is more preferable that the aromatic group substituted with at least three halogen atoms is an aromatic group substituted with at least three iodine atoms. In one preferred embodiment of the present invention, the aromatic group aromatic group substituted with at least two halogen atoms is 2,3,5-triiodobenzene.

In one embodiment of the present invention, the radiographic contrasting agent of formula (I) has the following structure:

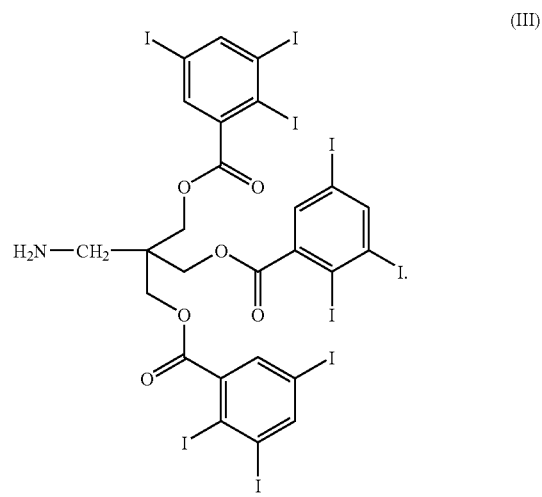
(III)

In another embodiment of the present invention, the inventive radiographic contrasting agent has one of the following structures:

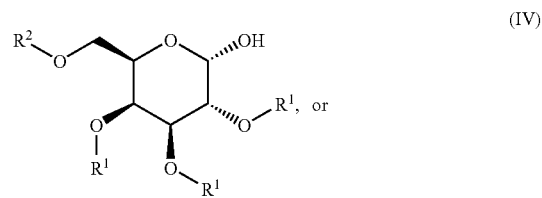
(IV)

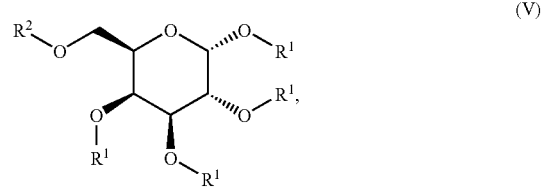
(V)

wherein

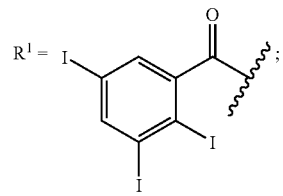

$R^1 =$

-continued

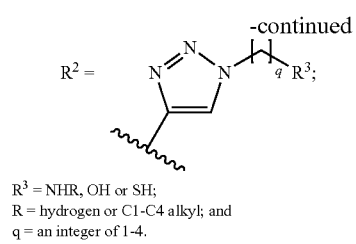

R³ = NHR, OH or SH;
R = hydrogen or C1-C4 alkyl; and
q = an integer of 1-4.

The radiographic contrasting agent of the present invention can be prepared through reactions between an organic compound containing polyhydric alcohol or polyamine and an aromatic compound substituted with multiple halogen atoms.

In one embodiment of the present invention, the radiographic contrasting agent of the present invention is first synthesized in its protected form through an esterification of a polyhydric alcohol and 2,3,5-triiodobenzoic acid chloride, as shown in Scheme 1. The protection group may be any protection groups that are suitable for protecting amines and compatible with the esterification process. Preferably, the protection group is a base-liable protection group, such as N-9-fluorenylmethyloxycarbonyl (Fmoc). The term "DMAP" as used herein denotes 4-(dimethylamino) pyridine or a hydrochloride salt thereof.

Scheme 1:

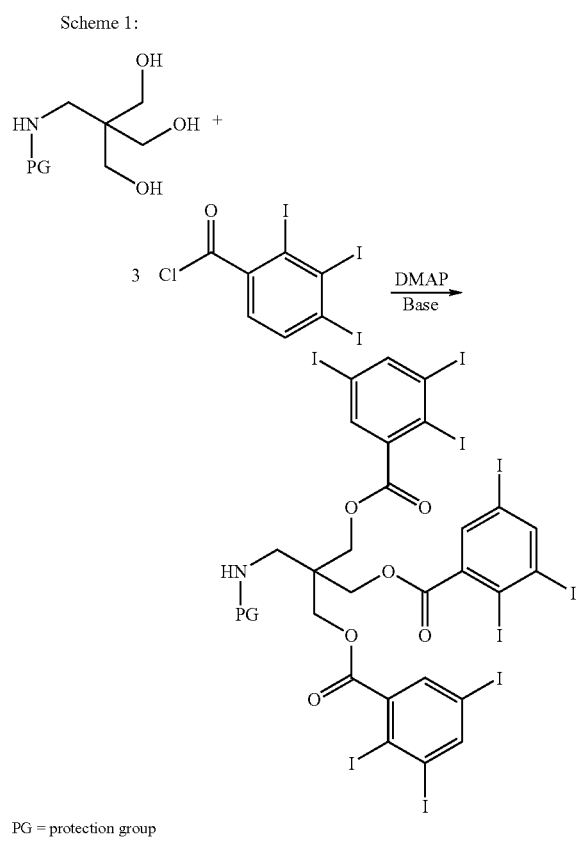

PG = protection group

Then the protection group is removed by a deprotection process providing the inventive radiographic contrasting agent, as shown in Scheme 2. The reaction condition of the deprotection process is determined by the nature of the protection group. For a base-liable protection group, the deprotection is typically conducted in the presence of a strong base.

Scheme 2:

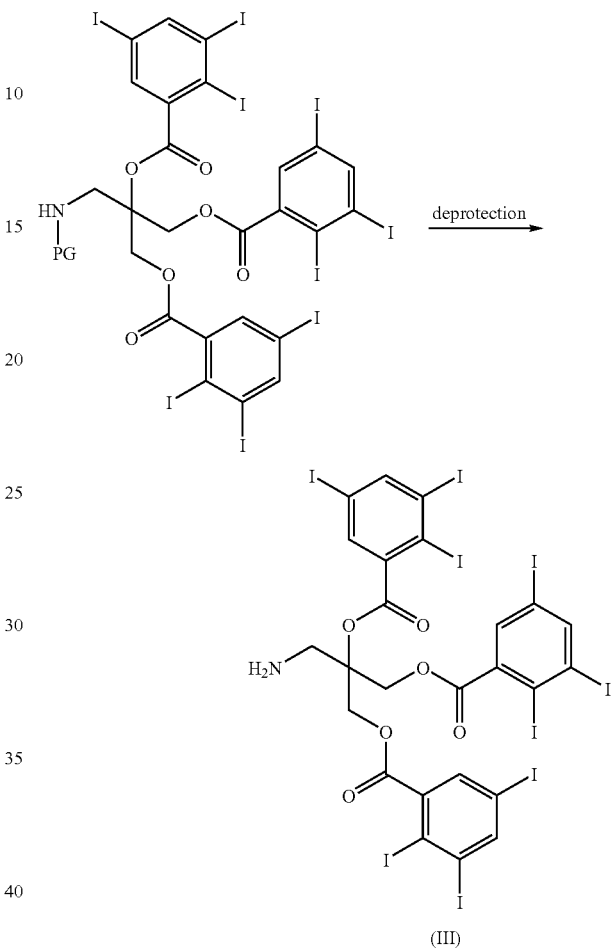

PG = protection group

In another embodiment of the present invention, the inventive radiographic contrasting agent is prepared from a monosaccharide through a Huisgen [3+2]cycloaddition under mild conditions, as illustrated in Scheme 3. Since the monosaccharide is non-synthetic, natural molecule containing polyhydric alcohol, the inventive radiographic contrasting agent derived therefrom has enhanced biocompatibility. As used herein, the term "TEA" denotes triethylamine.

Scheme 3:

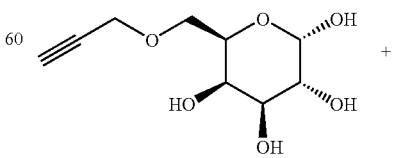

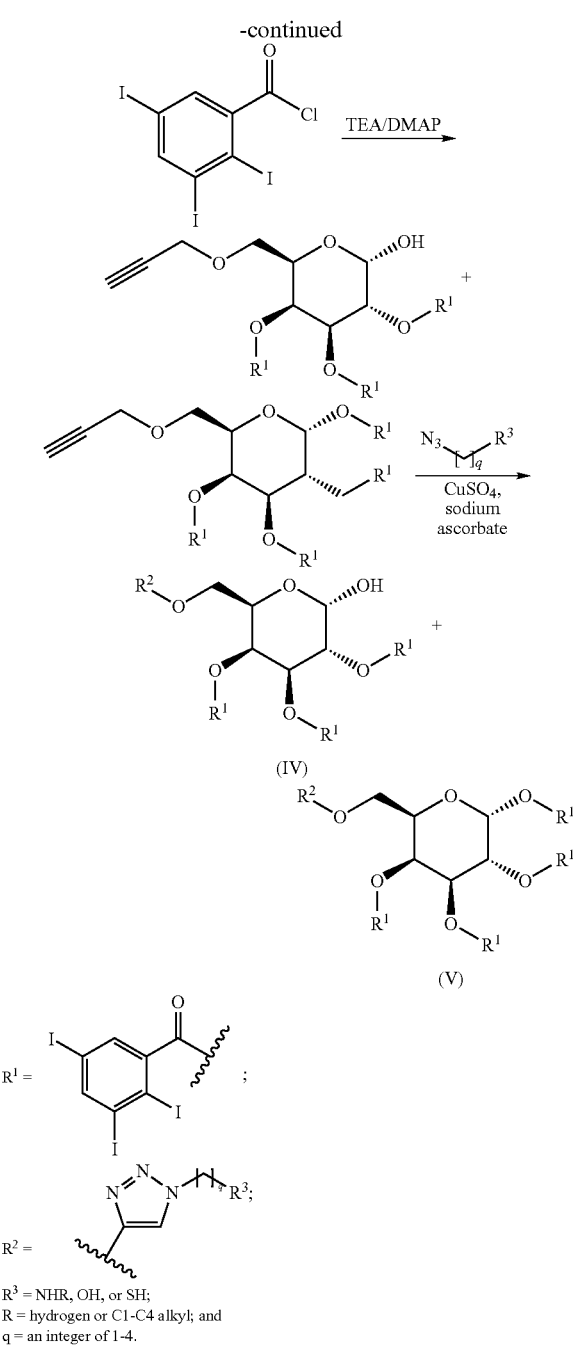

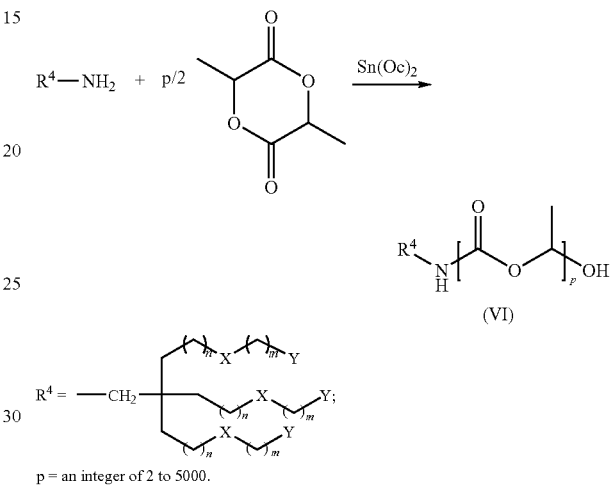

colide, polylactide, polydioxane, polycaprolactone, poly(lactide-co-glycolide), polyhydroxybutyrate, poly(trimethylene carbonate), other poly esters, and a mixture thereof.

In one embodiment of the present invention, the inventive radiographic contrasting agent of formula (I) initiates the ring-opening polymerization of lactide producing a polylactide having the radiographic contrasting agent attached thereto, as shown in Scheme 4. The term "$Sn(Oc)_2$" as used herein denotes stannous octoate. X, Y, n and m are the same as defined hereinbefore.

Scheme 4:

p = an integer of 2 to 5000.

The present invention also provides a radio-opaque polymeric material comprising a biodegradable polymer having at least one radiographic contrasting moiety covalently attached thereto. The at least one radiographic contrasting moiety is covalently attached to the biodegradable polymer through a functional group derived from a nucleophilic reaction. The at least one radiographic contrasting moiety comprises a monosaccharide backbone or an aliphatic or alicyclic backbone of 2 to 12 carbon atoms and at least two halogen-substituted aromatic groups. Each of the at least two halogen-substituted aromatic groups is substituted with at least three halogen atoms and is covalently attached to the monosaccharide backbone or the aliphatic or alicyclic backbone through a linkage group, wherein the linkage group is selected from oxygen, sulfur, —NH—, —O(CO)—, —(CO)O—, —NH(CO)—, —(CO)NH—, —O($SO_2$)—, —($SO_2$)O—, —O(SO)—, —(SO)O—, —NH($SO_2$)—, —($SO_2$)NH—, —NH(SO)—, —(SO)NH—, and triazole. The term "a nucleophilic reaction" as used herein denotes a chemical reaction between a reactive nucleophilic group and a carbonyl group. The term "a functional group derived from a nucleophilic reaction" as used herein denotes a functional group formed through a nucleophilic reaction between a reactive nucleophilic group and a carbonyl group. By "a reactive nucleophilic group", it is meant a reactive chemical moiety having an affinity to atomic nuclei. Reactive nucleophilic groups suitable for the present invention include, but are not limited to: NRH, OH, and SH; wherein R is a hydrogen atom or an alkyl group having 1 to 4 carbon atoms.

The reactive nucleophilic group in the inventive radiographic contrasting agent may react with an electrophilic group (e.g., a carbonyl group) in a biodegradable monomer initiating a polymerization process. Thus, the inventive radiographic contrasting agent may be an initiator for the polymerization of a biodegradable monomer producing a biodegradable polymer having the initiator, i.e., the inventive radiographic contrasting agent, covalently attached thereto. By "biodegradable polymer", it is meant a polymer that can be degraded or decomposed by natural biological processes, as by the action of bacteria, plants, or animals. Biodegradable polymers are also known as bioabsorbable polymers or biodissolvable polymers. Biodegradable polymers suitable for the present invention include, but are not limited to: polyglycolide, polylactide, polydioxane, polycaprolactone, poly(lactide-co-glycolide), polyhydroxybutyrate, poly(trimethylene carbonate), other poly esters, and a mixture thereof.

Preferably, the radiographic contrasting moiety in the inventive radio-opaque polymeric material has the following structure:

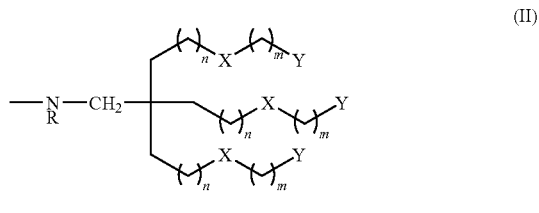

(II)

wherein R is a hydrogen atom, or an alkyl group having 1 to 4 carbon atoms;

X is oxygen, sulfur, —NH, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, or triazole; Y is an aromatic group substituted with at least three halogen atoms; n and m are the same or different, and are independently zero or an integer of 1 to 4. Preferably, R is a hydrogen atom; and X is —O(CO)—, —NH(CO)—, or triazole. More preferably, R is a hydrogen atom; X is —O(CO)—, —NH(CO)—, or triazole; and n and m are both zero. It is preferable that the aromatic group substituted with at least three halogen atoms is a benzene group substituted with at least three halogen atoms. It is also preferable that the at least three halogen atoms are bromine, iodine, or combinations thereof. It is more preferable that the aromatic group substituted with at least three halogen atoms is an aromatic group substituted with at least three iodine atoms. In one preferred embodiment of the present invention, the aromatic group aromatic group substituted with at least two halogen atoms is 2,3,5-triiodobenzene.

In the present invention, the biodegradable polymer having at least one radiographic contrasting moiety covalently attached thereto may be synthesized by initiating the polymerization of a biodegradable monomer with the inventive radiographic contrasting agent. The reactive nucleophilic group in the inventive radiographic contrasting agent can react with a carbonyl group in the biodegradable monomer forming a functional group and further initiating a polymerization process. The biodegradable polymer having at least one radiographic contrasting moiety covalently attached thereto comprises monomer units that include, but are not limited to: glycolide, lactide, dioxane, caprolactone, trimethylene carbonate, hydroxybutyrate, and combinations thereof. Therefore, the inventive biodegradable polymer can be readily prepared from common biodegradable monomers, such as lactide, glycolide, caprolactone, dioxane, trimethylene carbonate, hydroxybutyrate, or combinations thereof. In one embodiment of the present invention, the biodegradable polymer having at least one radiographic contrasting moiety is prepared through the synthetic route shown in Scheme 4. Preferably, the inventive biodegradable polymer having at least one radiographic contrasting moiety contains at least two radiographic contrasting moieties, thereby having enhanced radiographic contrasting effect. The inventive biodegradable polymer having at least two radiographic contrasting moieties can be synthesized by end-capping an inventive biodegradable polymer having one radiographic contrasting moiety with a derivative of the radiographic contrasting agent of formula (I), (IV), or (V).

In one embodiment of the present invention, the inventive radiographic contrasting agent is transformed to an acid derivative thereof, as shown in Scheme 5. X, Y, n, and m are the same as defined hereinbefore.

Scheme 5:

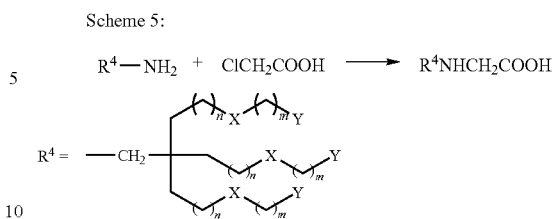

Next, the inventive biodegradable polymer of formula (VI) is end-capped with the acid derivative of the inventive radiographic contrasting agent providing an inventive biodegradable polymer having at least two radiographic contrasting moieties, as shown in Scheme 6. The term "DMAP" as used herein denotes 4-(dimethylamino) pyridine or a hydrochloride salt thereof. X, Y, n, and m are the same as defined hereinbefore.

Scheme 6:

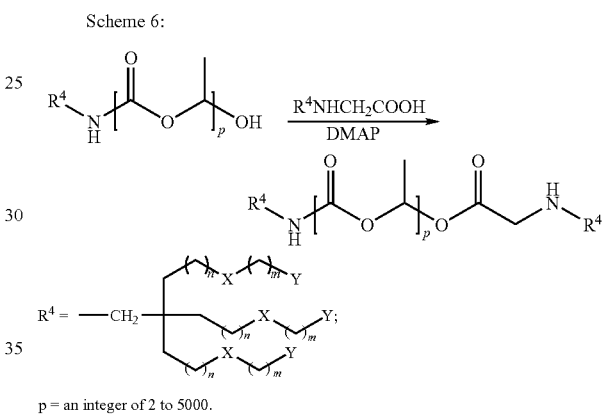

p = an integer of 2 to 5000.

The inventive biodegradable polymer not only possesses the desirable biocompatibility and physicomechanical properties (e.g., strength, fatigue, and smoothness), but also has radio-opacity for visualization in radiographic imaging. The mechanical strength and the degradation time of the inventive biodegradable polymer can be tuned by adjusting the molecular weight or composition thereof. The radiographic contrast intensity of the inventive biodegradable polymer can be adjusted by varying the ratio of the at least one radiographic contrasting moiety in the inventive biodegradable polymer or modifying the structure of the at least one radiographic contrasting moiety. The inventive biodegradable polymer is soluble in organic solvents and miscible with the bulk polymeric materials used to construct a medical device. The inventive biodegradable polymer is not soluble in water and do not leach out during the manufacture process or initial implantation period. Therefore, the inventive radio-opaque biodegradable polymer is suitable for the fabrication and use of medical devices interfacing with biological tissues, particularly implantable medical devices. Using similar reaction schemes as shown in Schemes 4 to 6, monosaccharide-based radiographic contrasting agents can be employed as polymerization initiators to prepare the inventive biodegradable polymers.

In another aspect, the present invention provides a medical device, wherein at least one portion of the medical device is radio-opaque. The at least one radio-opaque portion of the medical device comprises a radio-opaque polymeric material, which comprises a biodegradable polymer having at least one radiographic contrasting moiety covalently attached thereto. The at least one radiographic contrasting moiety is covalently attached to the biodegradable polymer through a functional group derived from a nucleophilic reaction. The at least one radiographic contrasting moiety comprises a monosaccharide backbone or an aliphatic or alicyclic backbone of 2 to 12 carbon atoms and at least two halogen-substituted aromatic groups. Each of the at least two halogen-substituted aromatic groups is substituted with at least three halogen atoms and is covalently attached to the monosaccharide backbone or the aliphatic or alicyclic backbone through a linkage group, wherein the linkage group is selected from oxygen, sulfur, —NH—, —O(CO)—, —(CO)O—, —NH(CO)—, —(CO)NH—, —O(SO$_2$)—, —(SO$_2$)O—, —O(SO)—, —(SO)O—, —NH(SO$_2$)—, —(SO$_2$)NH—, —NH(SO)—, —(SO)NH—, and triazole.

In one embodiment of the present invention, the at least one radiographic contrasting moiety has the following structure:

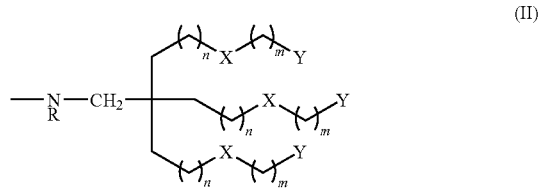

wherein R is a hydrogen atom, or an alkyl group having 1 to 4 carbon atoms;

X is oxygen, sulfur, —NH, —O(CO)—, —(CO)O—, —NH(CO)—, —(CO)NH—, —O(SO$_2$)—,

—(SO$_2$)O—, —O(SO)—, —(SO)O—, —NH(SO$_2$)—, —(SO$_2$)NH—, —NH(SO)—, —(SO)NH—, or triazole; Y is an aromatic group substituted with at least three halogen atoms; n and m are the same or different, and are independently zero or an integer of 1 to 4. Preferably, R is a hydrogen atom; and X is —O(CO)—, —NH(CO)—, or triazole. More preferably, R is a hydrogen atom; X is —O(CO)—, —NH(CO)—, or triazole; and n and m are both zero. Preferably, the inventive biodegradable polymer having at least one radiographic contrasting moiety covalently attached thereto contains at least two radiographic contrasting moieties, thereby having enhanced radiographic contrasting effect. Biodegradable polymers suitable for the present invention comprise monomer units that include, but are not limited to: glycolide, lactide, dioxane, caprolactone, trimethylene carbonate, hydroxybutyrate, and combinations thereof.

In the present invention, the radio-opaque portion of the medical device may be at least a portion of one surface of the medical device, a component of the medical device, or a portion of a component of the medical device. The radio-opaque portion of the medical device may be in any shape or size depending upon the intended use and the fabrication method of the medical device. When all surfaces of the medical device are covered with the inventive radio-opaque biodegradable polymeric material or the whole medical device is prepared from the inventive radio-opaque biodegradable polymeric material, the whole medical device is radio-opaque. Preferably, the medical device of the present invention is implantable. Examples of the medical devices suitable for the present invention include, but are not limited to: wound closure devices, such as, sutures, staples, and mesh; orthopedic fixation devices, such as, bone fracture fixation implants and bone augmentation implants; intestinal devices, such as, anastomosis rings and ligating clips; cardiovascular devices, such as, vascular grafts and drug elution stents; dental implants; nerve growth conduits; and other implantable medical devices. The inventive radio-opaque biodegradable polymeric material may be applied on at least a portion of one surface of a medical device using cast, spray, spin, dipping, or other methods known to one skilled in the art. The medical device or a component thereof can be constructed from the inventive radio-opaque biodegradable polymeric material using injection molding, compression molding, extrusion, or other methods know to one skilled in the art to construct polymeric medical devices.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

Having thus described our invention in detail, what I claim as new and desire to secure by Letters Patent is:

1. A radiographic contrasting agent having the following structure:

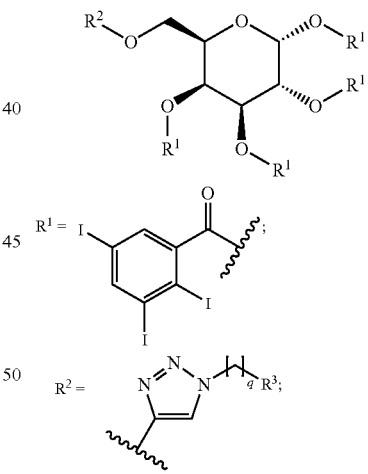

$R^3$ = NH$_2$, OH or SH; and
q = an integer of 1-4.

UNITED STATES PATENT AND TRADEMARK OFFICE
CERTIFICATE OF CORRECTION

| | | |
|---|---|---|
| PATENT NO. | : 7,771,705 B2 | Page 1 of 1 |
| APPLICATION NO. | : 12/412052 | |
| DATED | : August 10, 2010 | |
| INVENTOR(S) | : Jonathon Z. Zhao | |

It is certified that error appears in the above-identified patent and that said Letters Patent is hereby corrected as shown below:

On the front page of the patent, item (73) Assignee, delete "cordis" and insert -- Cordis --

Signed and Sealed this
Sixteenth Day of August, 2011

David J. Kappos
*Director of the United States Patent and Trademark Office*